United States Patent [19]

Rothgery

[11] 4,252,962

[45] Feb. 24, 1981

[54] PROCESS FOR PRODUCING 2-AMINO OR SELECTED 2-(SUBSTITUTED)AMINO-5-MERCAPTO-1,3,4-THIADIAZOLE COMPOUNDS

[75] Inventor: Eugene F. Rothgery, North Branford, Conn.

[73] Assignee: Olin Corporation, New Haven, Conn.

[21] Appl. No.: 132,966

[22] Filed: Mar. 24, 1980

[51] Int. Cl.³ ............................................. C07D 285/12
[52] U.S. Cl. ................................ 548/141; 260/455 R; 564/18
[58] Field of Search ......................................... 548/141

[56] References Cited

U.S. PATENT DOCUMENTS

| | | | |
|---|---|---|---|
| 2,708,670 | 5/1955 | Horclois et al. | 548/141 |
| 2,759,947 | 8/1956 | Song et al. | 548/141 |
| 2,891,961 | 6/1959 | Turner et al. | 548/141 |
| 3,865,739 | 2/1975 | Waldbillig | 548/141 |
| 4,066,436 | 1/1978 | Kirkpatrick | 548/140 |

OTHER PUBLICATIONS

Chemical Abstracts, vol. 55, col. 25991H and 25992a (1961).
Chemical Abstracts, vol. 52, col. 8189e and 12929d (1958).
Chemical Abstracts, vol. 47, col. 3342g (1953).

*Primary Examiner*—Alton D. Hollins
*Attorney, Agent, or Firm*—William A. Simons; Thomas P. O'Day

[57] ABSTRACT

Disclosed is a process for producing 2-amino or 2-(lower alkyl or phenyl)amino-5-mercapto-1,3,4-thiadiazole compounds by reacting the corresponding thiosemicarbazide with an alkali metal lower alkyl xanthate salt.

7 Claims, No Drawings

PROCESS FOR PRODUCING 2-AMINO OR SELECTED 2-(SUBSTITUTED)AMINO-5-MERCAPTO-1,3,4-THIADIAZOLE COMPOUNDS

BACKGROUND OF THE INVENTION

1. Field of the Invention

The present invention relates to a process for producing 2-amino or selected 2-(substituted)amino-5-mercapto-1,3,4-thiadiazoles.

2. Description of the Prior Art

2-Amino and many 2-(substituted)amino-5-mercapto-1,3,4-thiadiazoles have been found to be useful and important chemical intermediates in the synthesis of corrosion inhibitors, drugs, photographic chemicals and pesticides. For example, 2-(lower alkyl)amino-5-mercapto-1,3,4-thiadiazole compounds have been found useful as intermediates for herbicides. See U.S. Pat. No. 4,066,436 which issued to Kirkpatrick on Jan. 3, 1978.

In the past, there have been two reaction routes for producing these 1,3,4-thiadiazole compounds. One reaction route involves the reaction of thiosemicarbazide with carbon disulfide. See French Pat. No. 1,064,234, which issued to Horclois et al on May 12, 1954. This route is illustrated by the following equation (A) where 2-methylamine-5-mercapto-1,3,4-thiadiazole is prepared:

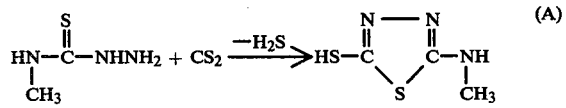

However, the carbon disulfide reactant is a particularly flammable material and requires specific facilities for its handling. Additionally, this method requires the use of organic solvents during the reaction which increase the production cost of the desired product.

The second known route for making these compounds involves the reaction of hydrazine with thiocyanates. See U.S. Pat. No. 2,966,495, which issued to Song et al on Dec. 27, 1960. This reaction is illustrated by equation (B) shown below, where 2-amino-5-mercapto-1,3,4-thiadiazole compounds are produced:

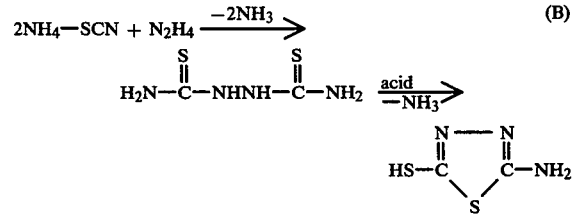

While these corresponding thiocyanates are commercially available, they are relatively expensive and the production cost of 1,3,4-thiadiazole compounds will be necessarily high.

BRIEF SUMMARY OF THE INVENTION

Accordingly, the present invention is directed to a method for producing 2-amino or 2-(substituted)amino 5-mercapto-1,3,4-thiadiazole compounds of the formula:

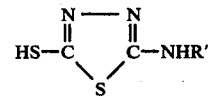

wherein R' is either hydrogen, a lower alkyl group having 1-4 carbon atoms, or phenyl which comprises reacting a corresponding thiosemicarbazide having the formula:

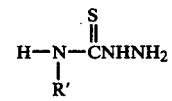

wherein R' is defined above, with an alkali metal lower alkyl xanthate salt of the formula:

wherein M is an alkali metal and R" is a lower alkyl group having from 1 to 4 carbon atoms.

DETAILED DESCRIPTION

The production of the above-noted 1,3,4-thiadiazole compounds by the process of the present invention is illustrated by the following equation (C) where 4-methylthiosemicarbazide is reacted with sodium ethyl xanthate to produce 2-methylamino-5-mercapto-1,3,4-thiadiazole:

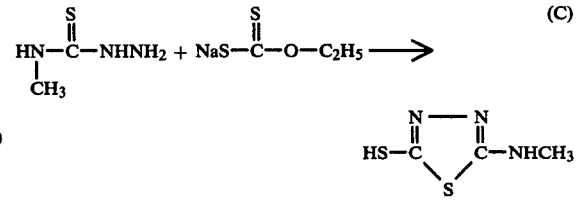

The thiosemicarbazide reactants may be conveniently prepared by several routes. For example, they may be prepared from hydrazine, $CS_2$ and either ammonia or the corresponding amine. See German Pat. No. 832,891, which issued to Klares et al on Mar. 3, 1952. Thiosemicarbazide may be also made by reacting hydrazine with ammonium thiocyanate. See U.S. Pat. No. 2,806,880 which issued to Kippur on Sept. 17, 1957. A list of suitable thiosemicarbazides for the present invention include:

thiosemicarbazide
4-methylthiosemicarbazide
4-ethylthiosemicarbazide
4-n-propylthiosemicarbazide
4-iso-propylthiosemicarbazide
4-n-butylthiosemicarbazide
4-iso-butylthiosemicarbazide
4-sec-butylthiosemicarbazide
4-tert.-butylthiosemicarbazide
4-phenylthiosemicarbazide The alkali methyl lower alkyl xanthate salts may be easily made by reacting the corresponding alkali metal hydroxide and lower alcohol with $CS_2$. See Rau, S. R. *Xanthates and Related Compounds*, Marcel Dekker, New York, 1971. Any alkali metal may be suitable in making these xanthate salts. A list of suitable and preferred alkali metal lower alkyl xanthate salts for the present invention include:

potassium or sodium methyl xanthate
potassium or sodium ethyl xanthate
potassium or sodium n-propyl xanthate
potassium or sodium iso-propyl xanthate
potassium or sodium n-butyl xanthate
potassium or sodium sec-butyl xanthate
potassium or sodium iso-butyl xanthate
potassium or sodium tert.-butyl xanthate In one preferred embodiment of the present invention, the corresponding thiosemicarbazide may be reacted with either potassium or sodium ethyl xanthate salt. These salts are both commercially available. The sodium ethyl xanthate salt is the most preferred, based on cost considerations.

The molar ratio of the two reactants is not critical to the present invention and any suitable ratio may be employed. Usually, it is desirable to avoid a large excess of either reactant since excess quantities would complicate the recovery of the desired 1,3,4-thiadiazole product. Preferably, the mole ratio of the thiosemicarbazide to the xanthate salt is from about 1.25:1 to about 1:1.5. More preferably, this molar ratio is in the range of from about 1.0:1.0 to about 1.0:1.1 in order to avoid a waste of excess reactant.

The reaction of the present invention may be preferably carried out in the presence of water. This is a major advantage of this invention since there are no expensive solvent removal and recovery systems necessary. However, the reaction will also proceed in organic solvents such as dimethylformamide (DMF), but this is less advantageous. The molar ratio of solvent to the reactants is not critical to the present invention and any suitable amount of solvent or solvents may be employed.

Other reaction parameters such as reaction temperatures, pressures, and times are generally not critical limitations of the present invention and this invention is not to be limited thereby. Any suitable reaction temperatures may be employed that result in a commercially acceptable yield. Preferably, reaction temperatures in the range from about 50° C. to about 100° C., more preferably from about 65° C. to about 95° C. may be utilized. Likewise, any suitable reaction pressure may be employed. Atmospheric pressure is most preferred because it does not reqire any special apparatus. Further, the reaction time for the present reaction normally may run from about 0.25 to 10 hours and will depend upon other factors such as reactant temperature, concentration of reaction and apparatus employed.

After the completion of the reaction, the desired product may be recovered by any conventional method. For example, it has been found that the addition of a sufficient amount of an acid (e.g., a mineral acid such as HCl) will precipitate substantially all of the desired product from the reaction mixture. Next, this precipitated product may be filtered from the mixture or removed by other conventional means. It may be desirable in some instances to further purify the recovered product by standard means like recrystallization techniques. The recovered product may be then used as an intermediate for uses stated above.

It should be noted that the present invention also contemplates the synthesis of other 2-amino analogs of 5-mercapto-1,3,4-thiadiazole by the present process.

The present invention is further illustrated by the following examples. All percentages and proportions are by weight unless otherwise explicitly indicated.

EXAMPLE 1

Production of 2-amino-5-mercapto-1,3,4-thiadiazole

Thiosemicarbazide (48 g, 0.5 mole) and technical grade potassium ethyl xanthate (85 g, 0.53 mole) were mixed in 250 ml of water. On heating to reflux, a black solution resulted. The mixture was refluxed 2.5 hours then cooled and acidified with concentrated hydrochloric acid to give a yellow solid. This crude product was filtered off, washed with water and dried giving 42.6 g (64% yield) of material melting at 215°–225° C. (lit. 232° C.) Recrystallization from ethanol, then from acetone raised the melting range to 232°–233° C.

Calculated for $C_2H_3N_3S_2$: C, 18.03; H, 2.25; N, 31.55; S, 48.14. Found: C, 18.22; H, 2.31; N, 31.30; S, 48.00.

EXAMPLE 2

Production of 2-methylamino-5-mercapto-1,3,4-thiadiazole

4-Methylthiosemicarbazide (52 g, 0.5 mole) and potassium ethyl xanthate (84 g, 0.52 mole) were mixed in 250 ml of water. On heating to 70° C. a clear, yellow solution resulted and at 94° C. the solution began to darken with the liberation of hydrogen sulfide. The solution was refluxed three hours, cooled in ice and acidified with concentration hydrochloric acid. A white precipitate formed which was filtered, washed with water and vacuum dried giving 34.5 g (47% yield) of product melting 181°–184° C.

Calculated for $C_3H_5N_3S_2$: C, 24.47; H, 3.42; N, 28.54; S, 43.56. Found: C, 24.34; H, 3.61; N, 28.34; S, 43.34.

What is claimed is:

1. A method for producing 2-amino or 2-(substituted) amino-5-mercapto-1,3,4-thiadiazole compounds of the formula:

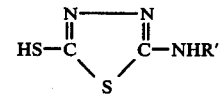

wherein R' is either hydrogen, a lower alkyl group having 1 to 4 carbon atoms, or phenyl which comprises reacting a corresponding thiosemicarbazide having the formula:

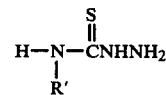

wherein R' is defined above, with an alkali metal lower alkyl xanthate salt having the formula:

wherein M is an alkali metal and R'' is a lower alkyl group having 1–4 carbon atoms.

2. The process of claim 1 wherein R' is hydrogen.
3. The process of claim 1 wherein R' is a lower alkyl having 1 to 4 carbon atoms.
4. The process of claim 3 wherein R' is methyl.
5. The process of claim 1 wherein R' is phenyl.
6. The process of claim 1 wherein said reaction occurs in the presence of water.
7. The process of claim 1 wherein M is sodium and R'' is ethyl.

* * * * *